United States Patent [19]

Reed, Jr. et al.

[11] Patent Number: 5,254,114
[45] Date of Patent: Oct. 19, 1993

[54] MEDICAL LASER DELIVERY SYSTEM WITH INTERNALLY REFLECTING PROBE AND METHOD

[75] Inventors: Edward D. Reed, Jr.; James R. Kermode, both of Sunnyvale; Dennis C. Frezzo, San Francisco, all of Calif.

[73] Assignee: Coherent, Inc., Palo Alto, Calif.

[21] Appl. No.: 745,269

[22] Filed: Aug. 14, 1991

[51] Int. Cl.5 .............................................. A61N 5/06
[52] U.S. Cl. ...................................... 606/15; 606/16; 606/17
[58] Field of Search ......................................... 606/2-7, 606/10-17; 128/395, 397, 398

[56] References Cited

U.S. PATENT DOCUMENTS

| | | | |
|---|---|---|---|
| 4,445,892 | 5/1984 | Hussein et al. | 604/101 |
| 4,648,892 | 3/1987 | Kittrell et al. | 65/4.21 |
| 4,672,961 | 6/1987 | Davies | 128/303 |
| 4,830,460 | 5/1989 | Goldenberg | 606/7 |
| 5,129,895 | 7/1992 | Vassiliadis et al. | 606/4 |

OTHER PUBLICATIONS

Selective Photothermolysis: Precise Microsurgery by Selective Absorption of Pulsed Radiation; by Anderson et al.; Science vol. 220 29 Apr. 1983 pp. 524-527.

T. G. van Leeuwen, M. J. van der Veen, R. M. Verdaasdonk, & C. Borst, "Noncontact Tissue Ablation by Holmium:YSGG Laser Pulses in Blood," 1991, *Laser in Surgery and Medicine*, 11:26-34, 9 pages in length.

*Primary Examiner*—David M. Shay
*Attorney, Agent, or Firm*—Limbach & Limbach

[57] ABSTRACT

A medical laser delivery system is disclosed which includes a laser generating a high power, pulsed, treatment beam. The beam is coupled to an optical fiber which is placed adjacent to a tissue site immersed in a fluid medium. The wavelength of the laser light and the energy of the pulses is selected so that the fluid medium will be quickly vaporized creating a vapor bubble around the end of the fiber. The end surface of the fiber is angled in a manner such that after the vapor bubble is formed, the laser output will be totally internally reflected at the end surface and be redirected out of the side of the fiber.

18 Claims, 3 Drawing Sheets

MEDICAL LASER DELIVERY SYSTEM WITH INTERNALLY REFLECTING PROBE AND METHOD

TECHNICAL FIELD

The subject invention relates to a medical laser system for delivering laser energy to a treatment site. The system includes a probe having an angled delivery end for redirecting the treatment beam out of the side of the probe.

BACKGROUND OF THE INVENTION

The use of lasers in medical procedures has increased significantly in the last few years. Medical laser devices include a laser engine for generating a high power treatment beam. A means is provided for delivering the treatment beam to the treatment site. The type of delivery means is dependent upon the wavelength of the laser radiation. For example, optical fibers have been developed to carry wavelengths in the visible and near infrared regions of the spectrum.

In most fiber delivery systems, the laser output exits the fiber substantially along its longitudinal axis. Fiber delivery systems have also been developed wherein the output beam is redirected so that it exits the probe at an angle relative to the axis of the fiber. By redirecting the angle of the beam, treatment sites can be reached which are not in line with the fiber. In addition, the probe can be used in a manner more similar to a mechanical knife.

One approach for redirecting the beam is to place a mirrored surface or a prism beyond the end of the fiber. Examples of such approaches can be found in U.S. Pat. Nos. 4,445,892 and 4,672,961.

Another approach is to utilize the phenomenon of total internal reflection to redirect the output beam. For example, in U.S. Pat. No. 4,648,890, there is disclosed a probe which has a specially configured tip located beyond the end of the fiber. The tip includes a small chamber filled with air having an index of refraction significantly lower than the material which forms an angled surface at the tip. The laser beam is reflected off the angled surface due to the differences in the indices of refraction of the tip material and the air pocket.

A related approach is described in copending application Ser. No. 07/560,201, filed Jul. 31, 1990, and incorporated herein by reference. This application describes a probe having an integrally formed angled end surface. A sealing member is provided and surrounds the end surface. The sealing member functions to trap air and exclude blood and saline from coming into contact with the angled end surface. Because of the difference in indices of refraction between the fiber and the air within the sealing member, the laser beam is totally internally reflected off the angled end surface and out the side of the fiber.

While the latter approach was effective for redirecting the light energy, it still required an extra sealing member. In addition, the sealing member is subject to failure under the harsh conditions associated with intense laser power.

Accordingly, it is an object of the subject invention to provide a new and improved laser delivery system which overcomes the problems associated with the prior art approaches.

It is a further object of the subject invention to provide a laser delivery system wherein the laser output is redirected out of the side of the optical fiber.

It is another object of the subject invention to provide a probe having only an angled end surface on the optical fiber which can nonetheless redirect laser light out of the side of the fiber.

SUMMARY OF THE INVENTION

In accordance with these and other objects, a medical laser system is provided which includes a laser for generating a treatment beam. The beam is delivered to the treatment site through an optical fiber mounted within a probe. The optical fiber has an input end and a delivery end. The treatment beam is coupled into the fiber through the input end and exits the delivery end.

In accordance with the subject invention, the delivery end of the fiber is provided with an angled end surface for redirecting the beam out of the side of the fiber. The angle of the end surface is selected so that the beam will undergo total internal reflection assuming that the medium surrounding the outside of the fiber has an index of refraction close to that of air.

In use, the probe is placed near the tissue to be treated. If the delivery end of the probe is surrounded by air, the treatment beam will be totally internally reflected and exit the side of the fiber. This effect is due solely to the angle of the end surface.

In many surgical procedures, the delivery end of the probe will be immersed in a liquid medium. The liquid medium might be blood or other natural body fluids. In the alternative, the area might be irrigated with saline. Since the index of refraction of these liquids is much closer to the index of refraction of the fiber, total internal reflection of the beam would not be expected. However, and in accordance with the subject invention, the wavelength and power of output pulses of the treatment beam are selected so that the water in the liquid medium surrounding the delivery end of the fiber will be vaporized. The vaporized liquid creates a bubble in the fluid medium that surrounds the fiber. The index of refraction of the bubble is substantially similar to the index of refraction of air. Thus, as soon as the bubble is formed, the treatment beam will be totally internally reflected at the angled surface and will exit the fiber along the side edge thereof.

The creation of the vapor bubble is based on the absorption of the laser energy by the fluid medium. The fluid media discussed above consist primarily of water. FIG. 1 is a logarithmic graph plotting the absorption coefficient (in units $cm^{-1}$) of laser energy in water with respect to wavelength. As can be seen, the absorption coefficient is significant above 1.5 microns and there are two absorption peaks at 2.1 microns and 3 microns. Applicants have tested the subject invention with a pulsed, high power, Ho:YAG laser with an output wavelength of 2.1 microns. The 2.1 micron output is closely matched to one of the absorption peaks in water. Ho:YAG pulses having an energy as low as 0.25 millijoule will create a bubble sufficient to redirect the light.

Other gain media which may be suitable to create this effect would include Thulium:YAG at 2.01 microns, Erbium:YAG at 2.9 microns and Nd:YAG, particularly at the 1.44 micron wavelength. As the wavelength of the laser output moves away from the absorption peaks in water, the energy per pulse needed to create the bubble will increase.

The creation of a vapor bubble at the end of a laser delivery probe in a liquid medium has been reported in "Noncontact Tissue Ablation by Holmium:YSGG Laser Pulses in Blood," *Lasers in Surgery and Medicine,* van Leeuwen et al, 11:26-34, (1991). As described in the article, the bubble begins to form as early as 15 microseconds into the pulse. In their device, the bubble reached its maximum extent at about 250 μs. The bubble then began to disintegrate and disappears by about 450 μs. In the preferred embodiment of the subject invention, the duration of the laser pulses are on the order of 300 μs, well within the window of existence of the bubble.

It should be noted that the discussion in the van Leeuwen article concerns the on-axis penetration depth of the laser beam and the role which the vapor bubble plays in increasing that depth. The article is unrelated to the use of such a bubble to create a total internally reflecting probe.

As can be appreciated, using the subject approach, total internal reflection of the beam off an angled surface can be achieved without the use of any additional structural elements attached to the end of the fiber. By this arrangement, an extremely simple and reliable device can be manufactured and used.

Further objects and advantages of the subject invention will be appreciated from the following detailed description taken in conjunction with the drawings in which:

DETAILED DESCRIPTION OF THE PREFERRED EMBODIMENT

Figure 1:
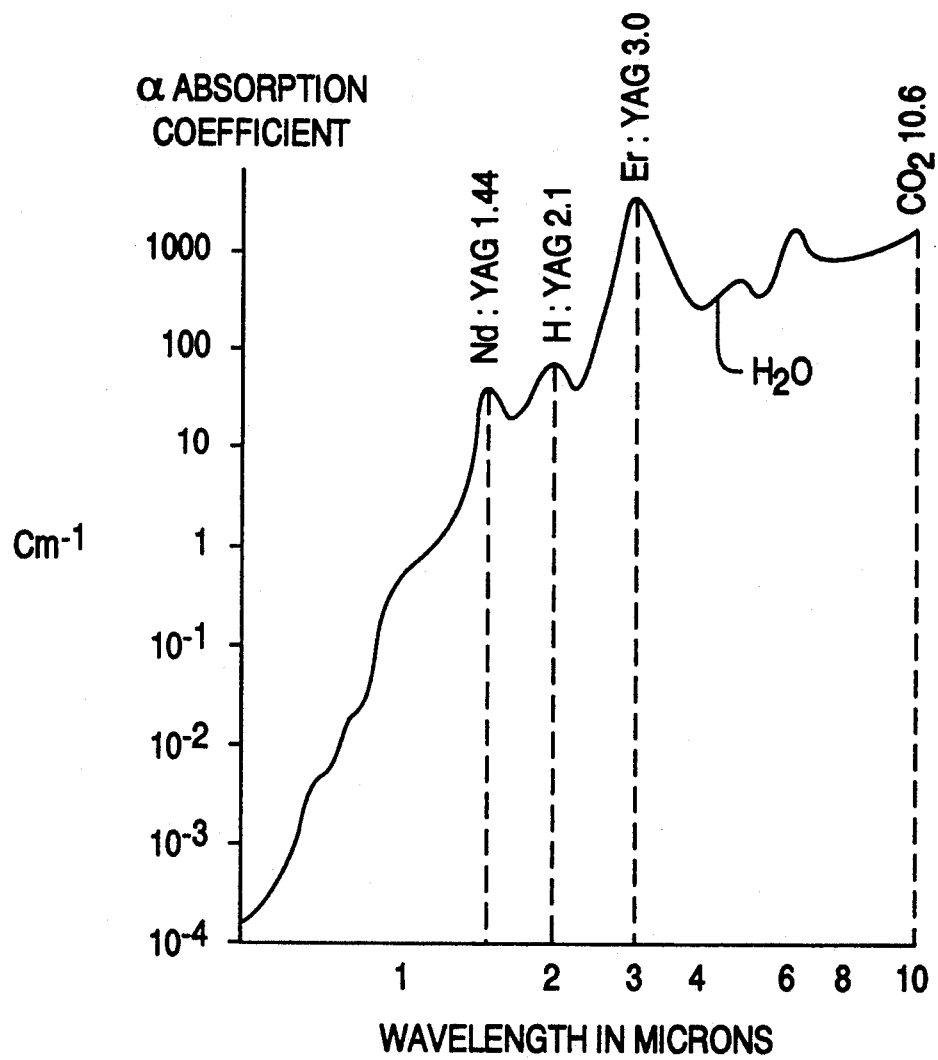
FIG. 1 is a graph illustrating the absorption of laser energy in water as a function of wavelength.
Figure 2:
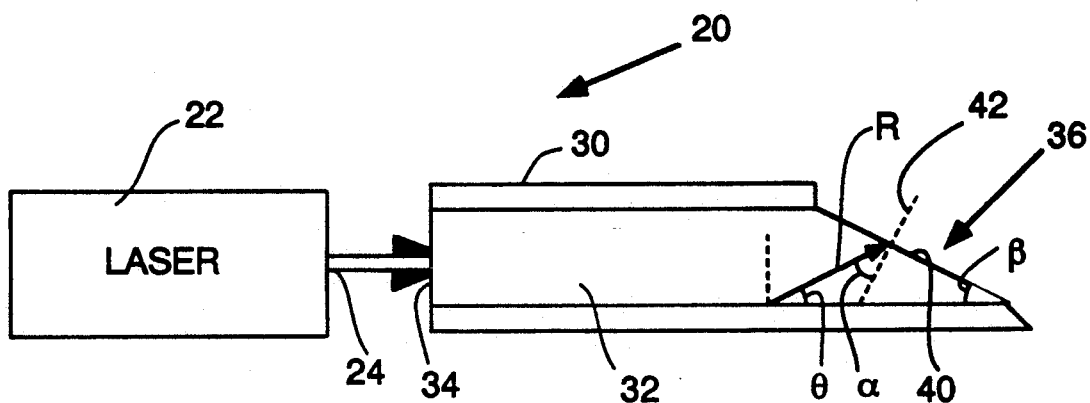
FIG. 2 is a schematic diagram of the subject system prior to the generation of a treatment pulse.
Figure 3:
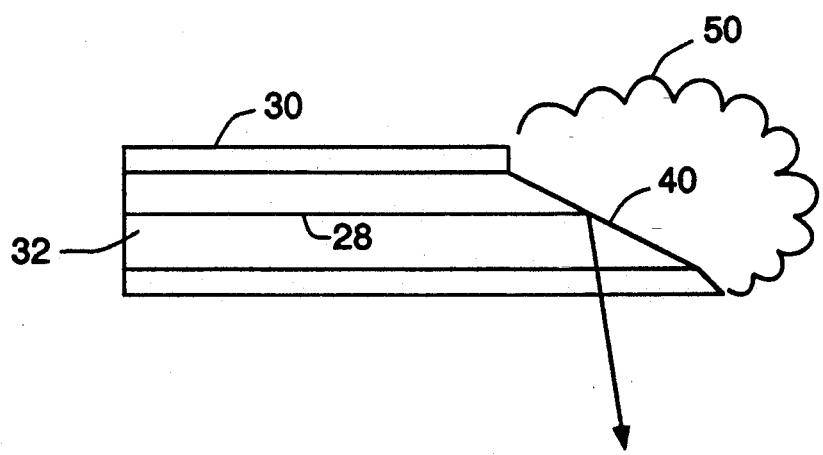
FIG. 3 is a schematic diagram of the subject invention during a treatment pulse.

Turning to FIGS. 2 and 3, there is illustrated a schematic view of the laser system 20 of the subject invention. The system 20 includes a laser source 22 for generating a treatment beam 24.

The subject invention further includes a probe 30. Probe 30 includes an optical fiber 32. The optical fiber 32 is typically formed from a glass. Fiber 32 has an input end 34 and a delivery end 36. The output beam from the laser 22 is coupled into the input end 34 of the fiber 32 with suitable optical elements.

In accordance with the subject invention, the delivery end 36 of the fiber includes an angled end surface 40. As in the above cited copending application, the angle $\beta$ is selected so that substantially all of the light output travelling down fiber 32 will be totally internally reflected at surface 40 and be redirected out the side of the fiber. This angle $\beta$ can be readily determined if indices of refraction of the fiber and the medium surrounding the fiber are known.

The approach for determining this angle $\beta$ begins with a determination of the angle of the ray R, relative to the surface normal 42, which must be met or exceeded to produce total internal reflection. The angle of total internal reflection (TIR) may be calculated using the following formula:

$$\alpha(TIR \text{ angle}) = \sin^{-1}(n_2/n_1) \quad 1)$$

where $n_1$ is the index of refraction of the fiber core and $n_2$ is the index of refraction of the medium surrounding the fiber. As will be discussed below, in the subject invention, the vapor bubble surrounding the end of the fiber will present a medium having an index substantially similar to air, which is close to unity.

The next step in the process is to determine the maximum angle $\theta$ along which rays will propagate within the fiber. While a portion of the rays will propagate close to the fiber's central axis, a significant portion of the energy will be guided off the walls of the fiber. The angle of maximum propagation $\theta$ is a function of the index of refraction of the material forming the core of the fiber versus the index of the refraction of the material forming the surrounding cladding and is given by the following formula:

$$\cos\theta = n_{clad}/n_{core} \quad 2)$$

The selection of the angle $\beta$ for the end surface is then made so that any rays propagating at maximum angle $\theta$ with respect to the axis of the fiber will equal the TIR angle ($\alpha$) when striking the end surface. All rays propagating along the fiber at less than the maximum propagation angle will exceed the TIR with respect to the end surface. Based on simple geometric principles, angle $\beta$ is then given by:

$$\beta = 90 - \alpha - \theta \quad 3)$$

In use, the probe 30 is inserted into the patient adjacent the site to be treated with the laser energy. The probe can be used in either a dry or a fluid environment. The fluid medium should consist primarily of water and be located around the delivery end of the fiber. The fluid medium can be blood or other body fluids. Alternatively, the fluid can be provided by irrigating the site with a saline solution. Saline irrigation is common in surgical procedures such as arthroscopic knee surgery.

Once the surgeon has positioned the fiber alongside the region to be treated, the high power treatment beam 24 can be activated. In accordance with the subject invention, the character of the treatment beam is such that if a fluid medium is present at the delivery end of the fiber, the fluid medium adjacent the end surface 40 will be vaporized creating a vapor bubble 50 as shown in FIG. 3. Once this vapor bubble 50 is created, the index of refraction on the outside of surface 40 will be similar to air and the treatment beam will be totally internally reflected and exit the side of the fiber.

As noted above, the creation of a vapor bubble at the end of a laser delivery fiber has been previously reported. It appears that the bubble begins to form very quickly, on the order of 15 μs. The length of time the bubble exists will be related to the time the laser energy is being transmitted through the fiber. Because the creation of the bubble is dynamic, and therefore a steady state could not be easily achieved, it is believed that the laser should be operated in a pulsed mode. The pulsed mode also has the advantage of increasing the peak power so that the water molecules will be rapidly vaporized.

As noted above, the power necessary to create the bubble is dependent on the absorption of the light in water and therefore the wavelength of the laser light. Applicants have successfully tested the subject invention using a pulsed Ho:YAG laser emitting a wavelength of 2.1 microns. Pulse energies as low as 0.25 millijoule are sufficient to create a vapor bubble that will cause the light to be totally internally reflected. Typical operating powers for arthroscopic knee procedures are in the range of one to two joules per pulse. Pulses in this range were generated having a duration of 300 $\mu$s which gave peak power levels on the order of 3000 to 6000 watts. In this range, the vapor bubble was created and lasted close to one millisecond so that substantially all of the pulsed power was totally internally reflected and redirected out of the side of the fiber. The laser was operated at 5 to 20 Hz.

Other wavelengths of light that are readily absorbed in water could be used to carry out the subject invention. The amount of power necessary to create the bubble is inversely proportional to the absorption of the light energy in the fluid medium. As noted above, thulium, erbium and neodymium would be suitable lasing species. These materials can be doped into various hosts such as YAG, YLF and YSGG. In the future, should a fiber be developed to safely carry longer wavelengths, other gain media, such as $CO_2$ at 10.6 microns could be used.

Figure 4:
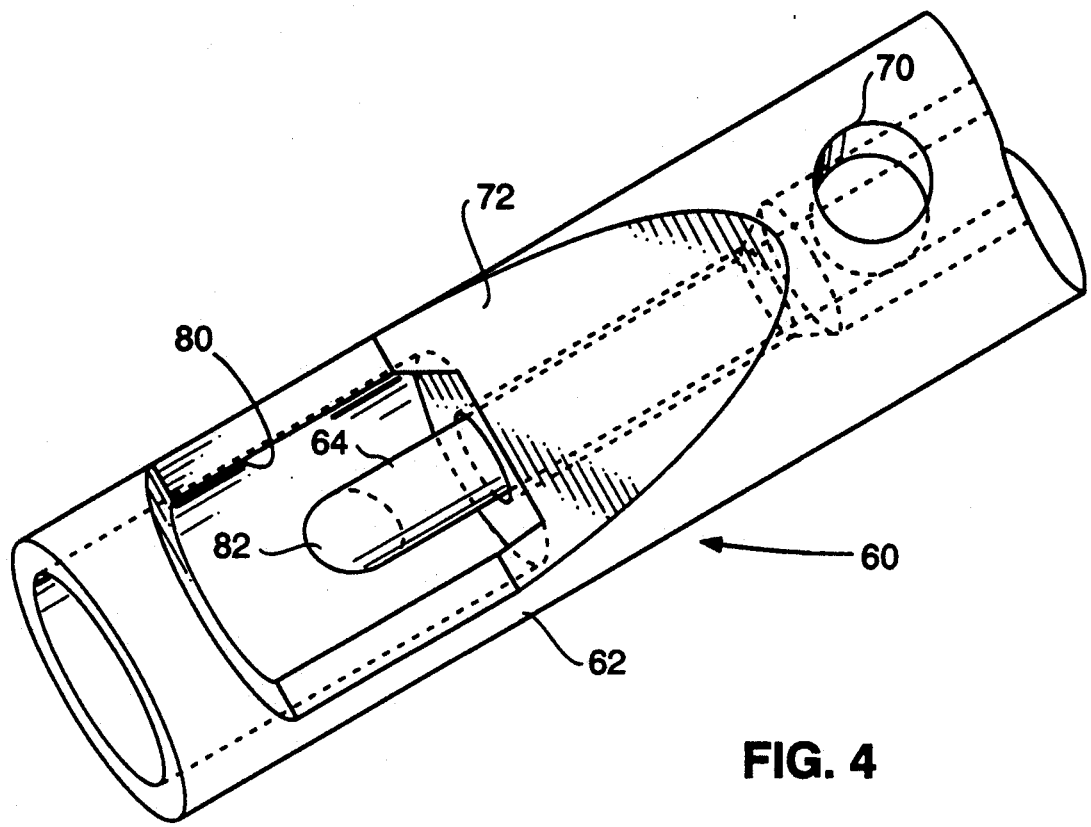
FIG. 4 is a perspective view of a probe formed in accordance with the subject invention.
Figure 5:
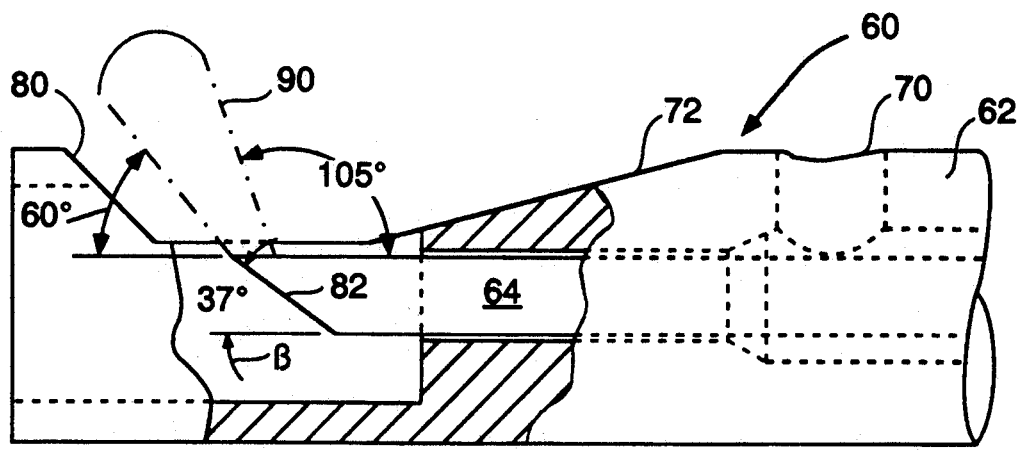
FIG. 5 is a cross-sectional view of the probe illustrated in FIG. 4.

FIGS. 4 and 5 illustrate a probe 60 which has been fabricated and tested in accordance with the subject invention. The probe consists of a holder 62 for surrounding and supporting the fiber 64. The fiber was formed from quartz having a 400 micron diameter core surrounded by a 40 micron thick layer of doped quartz cladding. The quartz fiber was surrounded by a silicone buffer layer and a nylon jacket. In order to increase the lifetime of the fiber, the buffer layer near the end of the fiber is stripped and the fiber is encased in an adhesive injected through hole 70. The end of the fiber is also polished and annealed. A tapered venting channel 72 is provided for venting vapor and debris from the end of the probe. The process of strengthening the fiber and providing venting channels is described in greater detail in copending application Ser. No. 07/584,287, filed Sep. 18, 1990, and incorporated herein by reference.

The end of the probe is provided with an opening 80 through which the treatment beam can be directed. In accordance with the subject invention, the end surface 82 of the fiber is angled in a manner to create total internal reflection of the treatment beam. It has been empirically determined that the optimum angle $\beta$ for the end surface is on the order of 37 to 38 degrees. This angle is consistent with the calculation set forth above using a 2.1 micron wavelength beam, a quartz fiber with a doped quartz cladding and assuming that the index of the vapor bubble is close to that of air. With the end surface set at about 37 degrees, the treatment beam 90 exits the fiber with a profile as illustrated in FIG. 5.

While the subject invention has been described with reference to a preferred embodiment, various changes and modifications could be made therein, by one skilled in the art, without varying from the scope and spirit of the subject invention as defined by the appended claims.

We claim:

1. A medical laser system for delivering laser energy to a treatment site in a liquid medium comprising:
    means for generating a laser output having a particular wavelength and energy level; and
    an optical fiber having a longitudinal axis and an input end and a delivery end, with the laser output being coupled to the input end and exiting the delivery end, and with the delivery end terminating in an end surface disposed at a non-normal angle with respect to the longitudinal axis of the fiber, said end surface being exposed to allow contact with the liquid medium, and with the wavelength and energy level of the laser output being selected such the output exiting the delivery end will vaporize the liquid medium in contact therewith creating a vapor bubble abutting said end surface and with the angle of said end surface being selected so that the laser output will be totally internally reflected off the end surface and be redirected out of the fiber in a direction transverse to the longitudinal axis of the fiber.

2. A system as recited in claim 1 wherein the end surface is oriented at an angle of 37 degrees with respect to the longitudinal axis of the fiber.

3. A system as recited in claim 1 wherein the end surface of the fiber is polished and annealed.

4. An apparatus as recited in claim 1 wherein said laser output is pulsed and has a wavelength of in the range of 1.44 to 2.9 microns.

5. A system as recited in claim 1 wherein said means for generating a laser output is a pulsed Ho:YAG laser, with each pulse having a duration.

6. A system as recited in claim 5 wherein the energy of each of said pulses exceeds 0.25 millijoules and wherein the duration of the pulses is 300 microseconds.

7. A system as recited in claim 1 wherein said laser output is pulsed, with each pulse having a duration.

8. A system as recited in claim 7 wherein the energy of each of said pulses exceeds 0.25 millijoule.

9. A system as recited in claim 7 wherein the duration of the pulses is 300 microseconds.

10. A system as recited in claim 9 wherein the energy of each of said pulses exceeds one joule.

11. A method for delivering laser energy to a treatment site in a liquid medium through a fiber wherein the fiber has a delivery end terminating in an end surface disposed at a non-normal angle with respect to the longitudinal axis of the fiber, with the end surface being in contact with the liquid medium, said method comprising:
    generating a laser output having a particular wavelength and energy level; and
    coupling the laser output into the fiber and with the wavelength and energy level of the laser output being selected such the output exiting the delivery end will vaporize the liquid medium in contact therewith creating a vapor bubble abutting the end surface whereby the laser output will be totally internally reflected off the end surface and be redirected out of the fiber in a direction transverse to the longitudinal axis of the fiber.

12. A method as recited in claim 11 wherein the step of generating includes generating a laser output with a particular pulse duration and having a wavelength in the range of 1.44 to 2.9 microns.

13. A method as recited in claim 11 wherein the step of generating includes generating a laser output with a particular pulse duration and energy per pulse and having a wavelength of 2.1 microns.

14. A method as recited in claim 13 wherein the energy of each pulse exceeds 0.25 millijoules and wherein the duration of the pulses is 300 microseconds.

15. A method as recited in claim 11 wherein the step of generating includes generating said laser output having a particular pulse duration.

16. A method as recited in claim 15 wherein the step of generating includes generating pulses with an energy which exceeds 0.25 millijoule per pulse.

17. A method as recited in claim 16 wherein the step of generating includes the step of generating said laser output having a pulse duration of 300 microseconds.

18. A method as recited in claim 17 wherein the step of generating includes the step of generating pulses with an energy exceeding one joule.

* * * * *